United States Patent [19]

Li

[11] Patent Number: 5,012,016

[45] Date of Patent: Apr. 30, 1991

[54] PROCESS FOR PREPARING TETRAPHENOLIC COMPOUNDS

[75] Inventor: Simon M. K. Li, Houston, Tex.

[73] Assignee: Shell Oil Company, Houston, Tex.

[21] Appl. No.: 495,980

[22] Filed: Mar. 20, 1990

[51] Int. Cl.$^5$ .................. C07C 39/12; C07C 37/20
[52] U.S. Cl. ..................... 568/720; 528/204
[58] Field of Search .................. 568/720; 528/204

[56] References Cited

U.S. PATENT DOCUMENTS

| | | | |
|---|---|---|---|
| 2,806,016 | 9/1957 | Schwarzer | 260/47 |
| 3,013,087 | 12/1961 | Schwarzer | 568/720 |
| 3,049,569 | 8/1962 | Apel et al. | 260/619 |
| 3,394,089 | 7/1968 | McNutt et al. | 260/2.2 |
| 4,415,724 | 11/1983 | Hedges et al. | 528/204 |
| 4,415,725 | 11/1983 | Mark et al. | 528/204 |
| 4,455,409 | 6/1984 | Faler et al. | 525/351 |
| 4,584,416 | 4/1986 | Pressman et al. | 568/727 |

FOREIGN PATENT DOCUMENTS

| | | | |
|---|---|---|---|
| 57-38814 | 3/1982 | Japan . | |
| 859456 | 1/1961 | United Kingdom | 568/720 |
| 883033 | 11/1961 | United Kingdom | 568/720 |
| 942594 | 11/1963 | United Kingdom | 568/720 |

Primary Examiner—Werren B. Lone

[57] ABSTRACT

Tetraphenolic compounds such as the tetraphenol of ethane and the tetraphenol of xylene can be prepared in a heterogeneous reaction mixture using an acidic cationic exchange resin catalyst. A continuous process can be most effectively carried out in the presence of an alcohol cosolvent for the reaction mixture.

18 Claims, No Drawings

PROCESS FOR PREPARING TETRAPHENOLIC COMPOUNDS

BACKGROUND OF THE INVENTION

This invention relates to the preparation of tetraphenolic compounds. In one aspect, the invention relates to a process for the continuous preparation of a tetraphenolic compound in a heterogeneous reaction mixture. In a specific embodiment, the invention relates to the continuous catalytic preparation of the tetraphenol of ethane from glyoxal and phenol.

Tetraphenolic compounds such as the tetraphenol of ethane are starting materials for the preparation of multifunctional epoxy resins for coatings and electronics applications. The tetraphenol of ethane can be prepared by the acid-catalyzed condensation reaction of glyoxal and phenol in a homogeneous liquid reaction mixture. Typical acid catalysts include aqueous hydrochloric acid and oxalic acid. When aqueous HCl is the catalyst for the reaction, a typical procedure is to neutralize the acidic reaction product mixture by addition of a base such as sodium hydroxide. The neutralized product mixture is then distilled for removal of excess phenol and by-products. The product yield of such a process is typically low, and the product is often contaminated with by-product from the sodium neutralizing agent. Use of strong acids also requires the use of special equipment including a glass-lined reactor, adding to the expense of the process.

It is therefore an object of the invention to provide a process for preparing tetraphenolic compounds. In one aspect, it is an object of the invention to provide a continuous heterogeneous process for the preparation of a tetraphenolic compound. In a further aspect, it is an object of the invention to improve product yield and purity in the preparation of the tetraphenol of ethane.

BRIEF SUMMARY OF THE INVENTION

According to the invention, a process is provided for preparing a tetraphenolic compound which can be described by the formula

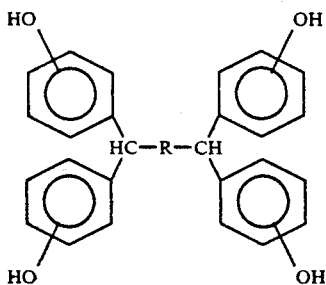

by contacting a dialdehyde with an equivalent excess of phenol in the presence of a cationic exchange resin catalyst. R in the above formula can be, for example, a direct bond, $C_{1-20}$ alkyl, aryl, and the like. The process is most suitably carried out in a continuous process in a reaction medium which includes a polar organic solvent.

DETAILED DESCRIPTION OF THE INVENTION

The starting materials for the condensation reaction in the preparation of a tetraphenolic compound are a dialdehyde and a phenolic compound. Suitable dialdehydes include compounds which can be represented by formula (1):

in which R is a direct bond or a hydrocarbyl linking moiety. R can be, for example, $C_{1-20}$ hydrocarbyl, including substituted and unsubstituted alkyl, aryl, alkaryl, aralkyl, cycloalkyl, and the like. Preferably, R is substituted or unsubstituted $C_{1-12}$ alkyl, aryl or alkaryl, particularly as represented structurally in formulas (2) and (3) below:

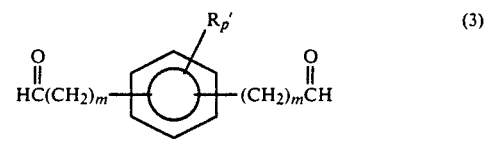

in which n is an integer from 0 to 12, m is an integer from 0 to 6, R' is a non-interfering substituent including $C_{1-4}$ alkyl and halide, and p is an integer from 0 to 4. Examples of such dialdehydes include glyoxal, glutaraldehyde, isophthalaldehyde and terephthalaldehyde.

The phenolic compound can be represented by formula (5):

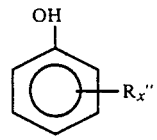

in which R" can be any substituent which does not interfere with the condensation reaction, including $C_{1-6}$ alkyl and halide, for example, and x is an integer from 0 to 5. Examples of such phenols include phenol, chlorophenol, fluorophenol and cresol.

The dialdehyde and the phenol are contacted in a reaction medium which includes an excess of phenol. Generally, the starting reaction medium will contain an equivalent ratio of phenol to dialdehyde of at least about 8:1, preferably within the range of about 8:1 to about 25:1, most preferably about 10:1 to about 15:1. The excess phenol will generally serve as a reaction diluent and the amount can be adjusted depending upon the presence of other solvents or diluents in the reaction mixture, and can be increased to help dilute the effect of excess water in the reaction mixture.

The dialdehyde and the phenol are reacted in the presence of an acidic cationic exchange resin catalyst. A number of cationic exchange resins having acid sites are known and commercially available. Preferable cationic exchange resins are slightly-crosslinked (0-4%) sulfonated styrene/divinylbenzene copolymers. Cationic exchange resins can include those which have a portion of the acid sites neutralized by mercaptoamine moieties such as those described in U.S. Pat. Nos. 3,394,089, 4,455,409 and 4,584,416, for example, although the unneutralized form is presently preferred for the preparation of tetraphenols. The presently preferred catalyst is a 2% divinylbenzene-crosslinked sulfonated polystyrene gellular resin. Such cationic exchange resins are available from Rohm & Haas under the designation XE-561, for example. Given the known sensitivity of such sulfonated ionic exchange resins to water (see, for example, U.S. Pat. No. 3,049,569, column 3, lines 52-59), it was surprising that they were effective in the synthesis of tetraphenols in reaction mixtures containing more than about 2% w water. The amount of water in the reaction mixture is particularly high in the preparation of the tetraphenol of ethane, which starts with glyoxal, currently available as a 40% w solution in water.

In the heterogeneous catalytic production of a tetraphenol, a dialdehyde and an excess of phenol are fed to a reaction vessel containing the cationic exchange resin catalyst. The reaction mixture is maintained at a temperature within the range of about 30° to about 110° C., preferably about 60° to about 95° C., for a time sufficient for preparation of the tetraphenol. The reaction is preferably carried out at atmospheric pressure. The reaction can be carried out in batch or continuous form. Under large-scale reaction conditions, continuous form will be preferred. The cationic exchange resin catalyst can be used as a slurry with the reactants in batch reactions or in a fixed bed in a continuous process. Two or more staged additions of the dialdehyde with interstage water evaporation can be employed to enhance yields.

The phenol can serve as a solvent for the reaction mixture. It is preferred, particularly for a continuous reaction, to carry out the reaction in the presence of an organic cosolvent. The organic solvent has been found to promote the solubility of impurities which may be present in the starting dialdehyde. Furthermore, in a continuous process, the presence of the cosolvent can prevent premature precipitation of the product or product intermediates as they form. Alcohols are the preferred organic cosolvents. Preferred alcohols, because of their availability and low cost, are $C_{1-8}$ alkanols such as methanol, isopropanol, ethanol and butanol, for example. If used, the cosolvent will generally be present in a weight ratio with respect to the dialdehyde of at least about 1:1, preferably within the range of about 1:1 to 10:1, most preferably about 1:1 to about 8:1.

The reaction time depends upon the reaction temperature and other reaction conditions. In a batch process, a reaction time within the range of about 0.1 to 20 hours will generally achieve desired conversion. In a continuous operation using a fixed catalyst bed, a flow rate with the range of about 0.1 to 12.0, preferably 0.5 to 8, weight per hour per bed weight will generally be suitable.

The product solution is then separated from the solid catalyst, and the tetraphenol is recovered by means such as flash distillation to remove any cosolvent, excess phenol, by-product water and other volatile impurities, and steam-stripping to remove unwanted oligomers or isomers. The tetraphenol can then be purified by subsequent steps such as recrystallization, solvent washing and the like. The product of the invention process will be a mixture of phenolic oligomers and isomers. The preferred technique for product recovery to maximize recovery of the tetraphenol product is to remove water and alcohol from the product mixture by distillation and then to cool the remaining solution to precipitate the tetraphenol. The phenol mother liquor from the precipitation step can then be recycled to the reaction mixture.

EXAMPLE 1

This example illustrates the batch preparation of the tetraphenol of ethane (TPE) in a heterogeneous reaction medium using a cationic exchange resin catalysts. Glyoxal, purchased as a 40% w solution in water, was mixed with 60 g phenol in a ratio of 1:25 (eq:eq), and the reaction mixture was heated to 180° F., whereupon about 6.2 g of the indicated catalyst was added. The catalysts used were 2% divinylbenzene-crosslinked sulfonated polystyrene ionic exchange resin in unmodified form, 10% bis(mercaptoethyl)amine-modified (BMEA) and 15% bis(mercaptoethyl)amine-modified, respectively. Samples of product were taken at the indicated times after catalyst addition and analyzed for molecular weight. Results are shown in Table 1.

TABLE 1

| Batch Synthesis of TPE | | | | | |
|---|---|---|---|---|---|
| Catalyst | Sampling Time Time (min.) | Mn+ | Mw+ | Mz+ | Q |
| Unmodified IER | 15 | 364 | 412 | 453 | 1.13 |
| | 60 | 314 | 377 | 433 | 1.20 |
| | 120 | 306 | 370 | 428 | 1.21 |
| | 360 | 294 | 360 | 422 | 1.23 |
| 10% BMEA Modified IER | 15 | 324 | 382 | 430 | 1.18 |
| | 60 | 296 | 362 | 421 | 1.22 |
| | 120 | 295 | 362 | 420 | 1.23 |
| | 360 | 295 | 360 | 419 | 1.22 |
| 15% BMEA Modified IER | 15 | 197 | 215 | 241 | 1.09 |
| | 60 | 285 | 352 | 436 | 1.24 |
| | 120 | 296 | 368 | 447 | 1.24 |
| | 360 | 300 | 384 | 475 | 1.28 |
| | * | 356 | 421 | 493 | 1.18 |

+ The "drop" in Mn, Mw and sometimes Mz at longer reaction times may be due to formation of additional monofunctional oligomer, which shifts the molecular weight distribution toward lower oligomers.
* After excess phenol was stripped from product reaction mixture.

EXAMPLE 2

This example illustrates the continuous preparation of the tetraphenol of ethane in a heterogeneous reaction medium using a cationic exchange resin catalyst. A series of experiments was performed at various reaction temperatures and ratios of reactants. Reactants were charged to a feed vessel and pumped via a metering pump through a fixed-bed reactor containing the ionic exchange resin catalyst. The catalyst was a 2% divinyl benzene-crosslinked sulfonated polystyrene ionic exchange resin. Sampels of product were taken after steady-state had been reached. Conditions and results are summarized in Table 2.

TABLE 2

| Continuous Synthesis of TPE | | | | | | | | | | | | | | |
|---|---|---|---|---|---|---|---|---|---|---|---|---|---|---|
| Temp, °C. | 85.00 | | 75.00 | | 85.00 | | 75.00 | | 85.00 | | 85.00 | | 85.00 | |
| % w Water, Titra. | 2.23 | 3.08 | 2.30 | 3.00 | 3.86 | 5.29 | 3.71 | 5.10 | — | — | 2.68 | 3.56 | 2.43 | 3.21 |
| P/G, eq/eq | 15.00 | | 15.00 | | 10.00 | | 10.00 | | 25.00 | | 12.00 | — | 12.00 | — |
| I/AG, w/w | 6.00 | | 6.00 | | 2.00 | | 2.00 | | 2.00 | | 6.00 | — | 6.00 | — |
| % w PhOH, Anal. | 74.77 | 69.60 | 74.40 | 70.54 | 81.65 | 73.37 | 82.98 | 75.86 | 90.13 | 87.06 | | | | |
| % Conv/PhOH (4M/1M) | | 54.33 | | 40.25 | | 52.20 | | 44.87 | | 42.81 | | 46.25 | | 39.76 |
| Avg Function., M/M | | 2.2 | | 1.6 | | 2.1 | | 1.8 | | 1.7 | | 1.8 | | 1.6 |
| % w TPE Prod, Theory | | 10.1 | | 10.1 | | 16.8 | | 16.8 | | 7.6 | | 11.9 | | 11.9 |

TABLE 2-continued

| | Continuous Synthesis of TPE | | | | | | | | | | | | |
|---|---|---|---|---|---|---|---|---|---|---|---|---|
| % w TPE, est/PhOH | 5.4 | | 4.1 | | 8.8 | | 7.5 | | 3.2 | | 5.5 | 4.7 |
| 1/WSHV, min | 29.8 | | 13.7 | | 33.8 | | 27.7 | | 27.6 | | 28.4 | 6.6 |
| Mn | 327 | | 308 | | 343 | | 302 | | 292 | | 313 | 288 |
| Mw | 413 | | 360 | | 402 | | 380 | | 360 | | 364 | 337 |
| Mz | 659 | | 419 | | 458 | | 442 | | 439 | | 406 | 398 |
| Q | 1.26 | | 1.17 | | 1.17 | | 1.18 | | 1.23 | | 1.16 | 1.17 |
| Temp, °C. | | | 75.00 | | | 65.00 | | 85.00 | | 85.00 | | 85.00 | |
| % w Water, Titra. | | 2.39 | 3.17 | | 2.40 | 2.98 | 3.49 | 4.41 | 3.27 | 3.74 | 3.20 | 4.13 |
| P/G, eq/eq | | 12.00 | — | | 12.00 | — | 8.00 | — | 8.00 | — | 8.00 | — |
| I/AG, w/w | | 6.00 | — | | 6.00 | — | 4.20 | — | 6.00 | — | 6.00 | — |
| % Conv/PhOH (4M/1M) | | | 55.10 | | | 27.41 | | 39.27 | | 24.91 | | 37.65 | |
| Avg Function.. M/M | | | 2.2 | | | 1.1 | | 1.0 | | 1.0 | | 1.5 | |
| % w TPE Prod, Theory | | | 11.9 | | | 11.9 | | 17.2 | | 15.4 | | 15.4 | |
| % w TPE, est/PhOH | | | 6.6 | | | 3.3 | | 6.8 | | 3.8 | | 5.8 | |
| 1/WSHV, min | | | 29.3 | | | 30.3 | | 6.6 | | 6.9 | | 30.0 | |
| Mn | | | 307 | | | 295 | | 282 | | 260 | | 272 | |
| Mw | | | 358 | | | 348 | | 350 | | 314 | | 332 | |
| Mz | | | 413 | | | 422 | | 510 | | 426 | | 474 | |
| Q | | | 1.17 | | | 1.18 | | 1.24 | | 1.21 | | 1.22 | |

EXAMPLE 3

This example illustrates the batch preparation of the tetraphenol of xylene [α,α,α',α'-tetrakis-(4-hydroxyphenyl)-p-xylene] using a cationic exchange resin catalyst. Terephthaldicarboxaldehyde (TDA) was received in dry crystalline form and dissolved in phenol at 50° C. 151 grams of a solution of TDA in phenol (1:15 molar ratio) was heated to 80° C. 15 grams of dry Lewatit SC-102 (2% divinylbenzene crosslinked ion exchange resin) were added and an exotherm was observed and controlled with air cooling. Samples were taken at 15 minutes, 30 minutes, 1 hour and 2 hours after IER addition. The solution color progressively turned from light yellow to orange to burgundy at apparent increased solution viscosity. After about 2 hours, solids began forming in the solution phase and the reaction was terminated. Addition of isopropyl alcohol (3:1 weight, based on starting TDA) dissolved the solids at 80° F. Filtrate separated from the IER was evaporated at up to 200° C. under vacuum.

Samples were analyzed by HPLC and GPC (both ultraviolet and refractive index). From the HPLC, it was concluded that the TDA was extensively reacted after 1 hour of contact time with the IER (approximately equivalent to 10 WHSV in a continuous mode of operation). At least four major product peaks were observed in the HPLC's. GPC-RI analysis indicated that the product consists predominantly of diphenolic oligomers, suggesting that the crystallized solid observed in the experiment at 2+ hours and 80° C. is mostly difunctional.

EXAMPLE 4

This experiment was performed to illustrate the effect of a cosolvent in the reaction mixture in the preparation of the tetraphenol of xylene. A reaction mixture as in Experiment 3 was prepared, with the exception that isopropyl alcohol was added (3:1 w/w to TDA) to attempt to depress solubility of the condensation products. At a phenol to TDA molar ratio of 20:1 and a 10:1 weight ratio of reaction mixture to IER, the reaction was allowed to proceed at 80° C. for 5 hours. After separation and additional extraction of the spent IER, the combined filtrate was evaporated under vacuum at 190° C. to give a 75% yield of product (based on 100% theoretical tetrafunctional product).

HPLC analysis of this product showed that two peaks observed in Experiment 3 were absent, suggesting that these peaks represented low molecular weight oligomers which advanced to higher molecular weight oligomers over the extended time of the experiment, made possible by the use of a cosolvent to solubilize intermediates. This conclusion was substantiated by GPC-RI, which indicated the substantial absence of monofunctional oligomer.

I claim:

1. A process for preparing a tetraphenol of the formula

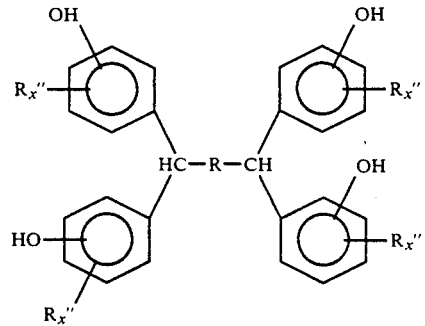

the process comprising contacting, in a reaction mixture at a temperature within the range of about 30° to about 120° C., a dialdehyde of the formula

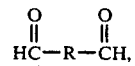

in which R is a direct bond or substituted or unsubstituted $C_{1-20}$ hydrocarbyl, and a stoichiometric excess of a phenolic compound which can be represented by the formula

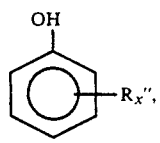

in which each R" is selected from noninterfering substituents and x is an integer from 0 to 5, in the presence of a catalytic amount of an acid-functional cationic exchange resin catalyst.

2. The process of claim 1 in which the dialdehyde can be represented by the formula

in which R is a direct bond or a substituted or unsubstituted $C_{1-20}$ hydrocarbyl.

3. The process of claim 2 in which the phenolic compound is phenol.

4. The process of claim 3 in which the phenol is present in a molar ratio to the dialdehyde of at least about 8:1.

5. The process of claim 4 in which the reaction temperature is within the range of about 45° to about 100° C.

6. The process of claim 4 in which the dialdehyde can be represented by the formula

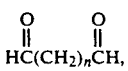

in which n is an integer selected from 0–12.

7. The process of claim 6 in which the dialdehyde is glyoxal.

8. The process of claim 1 in which the dialdehyde can be represented by the formula

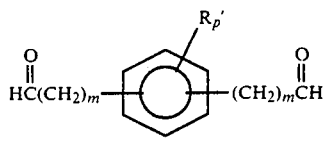

in which m is an integer within the range of 0 to 6, R' is a non-interfering substituent, and p is an integer from 0 to 4.

9. The process of claim 8 in which the phenolic compound is phenol.

10. The process of claim 9 in which the phenol is present in a molar ratio to the dialdehyde of at least about 8:1.

11. The process of claim 1 in which the reaction mixture further comprises an organic solvent.

12. The process of claim 11 in which the organic solvent comprises a $C_{1-8}$ alkanol.

13. The process of claim 12 in which the organic solvent comprises isopropyl alcohol.

14. The process of claim 1 in which the cationic exchange resin catalyst is a divinylbenzene-crosslinked sulfonated polystyrene ionic exchange resin.

15. The process of claim 14 in which the cationic exchange resin catalyst has a degree of divinylbenzene crosslinking no greater than about 4%.

16. The process of claim 1 in which each R'' is independently selected from $C_{1-6}$ alkyl and halide.

17. The process of claim 1 in which the phenolic compound is selected from the group consisting of phenol, chlorophenol, fluorophenol and cresol.

18. The process of claim 11 in which the organic solvent comprises methanol.

* * * * *